United States Patent [19]
Biere et al.

[11] 3,962,471
[45] June 8, 1976

[54] INDOLYLACETYLAMINO ACID DERIVATIVES, PROCESS FOR THEIR PREPARATION, AND PHARMACEUTICAL COMPOSITIONS

[75] Inventors: Helmut Biere; Hanns Ahrens; Clemens Rufer; Eberhard Schroder; Henning Koch, all of Berlin, Germany

[73] Assignee: Schering Aktiengesellschaft, Berlin & Bergkamen, Germany

[22] Filed: Mar. 12, 1975

[21] Appl. No.: 557,515

[30] Foreign Application Priority Data
Mar. 15, 1974 Germany.............................. 2413125

[52] U.S. Cl....................... 424/274; 260/326.12 A; 260/326.13 A; 260/326.14 A
[51] Int. Cl.²........................................ C07D 209/28
[58] Field of Search.......... 260/326.13 A, 326.14 A; 424/274

[56]                  References Cited
              UNITED STATES PATENTS
3,336,194    8/1967    Shen ........................... 260/326.13 A
3,669,960    6/1972    Okamoto et al. ........... 260/326.13 A
       FOREIGN PATENTS OR APPLICATIONS
47-44221    11/1972    Japan......................... 260/326.13 A

*Primary Examiner*—Lewis Gotts
*Assistant Examiner*—S. P. Williams
*Attorney, Agent, or Firm*—Millen, Raptes & White

[57]            ABSTRACT
Indolylacetylamino acids of the formula

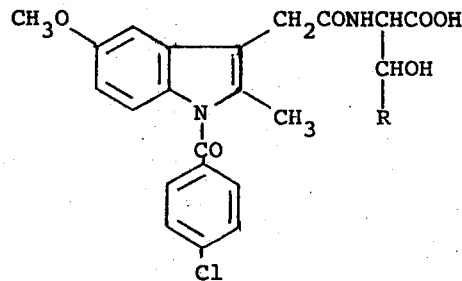

wherein R is H or $CH_3$, physiologically acceptable salts thereof and the corresponding amides, alkyl and benzyl esters and alkyl and benzyl ethers thereof, possess anti-inflammatory activity.

13 Claims, No Drawings

INDOLYLACETYLAMINO ACID DERIVATIVES, PROCESS FOR THEIR PREPARATION, AND PHARMACEUTICAL COMPOSITIONS

BACKGROUND OF THE INVENTION

This invention relates to novel indolylacetylamino acids and derivatives thereof and to processes for their production and use.

It is known that substituted 3-indolylacetic acids, for example, 1-(4-chlorobenzoyl)-5-methoxy-2-methyl-3-indolylacetic acid (indomethacin), have good anitinflammatory properties. Such compounds have, however, the known disadvantage of having a low therapeutic index. Even low dosages cause lesions in the stomach epithelium or stomach ulcers (Mathies, *Med. Klinik* 60, 1863–1869 (1965); Bhargava, K. P., *Europ. J. Pharmacol.* 22, 191–195 (1973); Green, D., P. G. Goode, and A. B. Wilson, 1969 Fourth International Congress on Pharmacology, Basel, Switzerland, p. 104; Somegyi, A., K. Kovacs, and H. Selye, *J. Pharma. Pharmacol.* 21, 122 (1969)).

U.S. Pat. No. 3,336,194 describes secondary and tertiary amides of the corresponding 3-indolylacetic acids which, however, have been proved to be less effective than indomethacin according to our own test findings. Japanese Patent 47-44,221 describes the methionine derivative of indomethacin which, however, also is less effective than indomethacin.

It is an objective of the present invention to provide novel compounds which have the effectiveness of indomethacin, which are better tolerated by the stomach and which have lower toxicity. Other objects will be apparent to those skilled in the art.

SUMMARY OF THE INVENTION

In a composition aspect, this invention relates to new indolylacetyl amino acid derivatives of the general Formula I

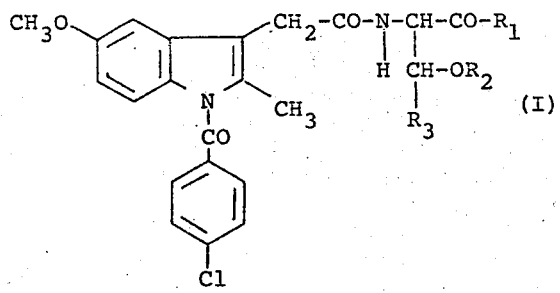

wherein $R_1$ is OH, $NH_2$, $NHR_4$ or $OR_4$ wherein $R_4$ is alkyl of 1–4 carbon atoms or benzyl, $R_2$ is a hydrogen atom, alkyl of 1–4 carbon atoms or benzyl, and $R_3$ is a hydrogen atom or methyl, and when $R_1$ is OH, the physiologically acceptable salts thereof with bases.

In another composition aspect, this invention relates to compositons comprising one or more compounds of Formula I in admixture with a pharmaceutically acceptable carrier.

In process aspects, this invention relates to processes for the production of such compounds and their use as antiinflammatory agents.

DETAILED DISCUSSION

Examples of classes of compounds of Formula I are those wherein a. $R_2$ is alkyl, preferably $CH_3$, especially those wherein $R_1$ is OH, $OR_4$ or $NHR_4$, preferably $OCH_3$ or $NHCH_3$, and most preferably OH and the physiologically acceptable salts thereof, preferably Na;

b. $R_2$ is H, preferably those wherein $R_1$ is OH, $OR_4$ or $NHR_4$, preferably $OCH_3$ or $NHCH_3$, and most preferably OH and the physiologically acceptable salts thereof, preferably Na; and c. $R_3$ is H, especially those of (a) and (b); and d. $R_3$ is $CH_3$, especially those of (a) and (b).

The compounds of Formula I have an asymmetrical carbon atom and, therefore, can be in the form of racemates or optical antipodes thereof.

The $R_2$ and $R_4$ alkyl groups preferably are methyl, ethyl, propyl, isopropyl, and tertiary butyl.

The compounds of this invention include the physiologically acceptable salts of compounds of Formula I wherein $R_1$ is H with bases, include metal salts, e.g., alkali-metal, preferably Na, and amine salts, e.g., of alkanolamines, dialkylamines, alicyclic amines and aminosugars.

In a process aspect, this invention relates to a process for preparing the indolyacetyl amino acid derivatives of Formula I, by a. the reaction in a convention manner of an activated derivative of 1-(4-chlorobenzoyl-5-methoxy-2-methyl-3-indolylacetic acid of general Formula II

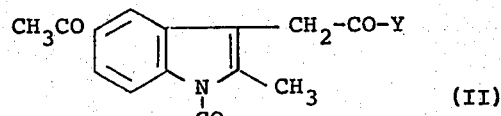
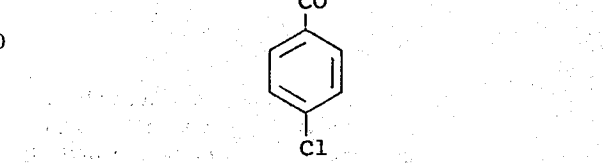

wherein Y is an activating radical, with a serine derivative of general Formula III

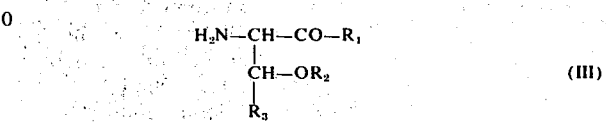

wherein $R_1$, $R_2$, and $R_3$ have the values given above, or a salt or the free acid; or b. the reaction in a conventional manner of an indolylacetyl amino acid derivative of general Formula IV

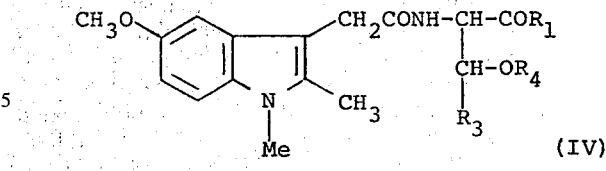

wherein $R_1$ and $R_3$ have the values given above, and $R_4$ is a hydrogen atom, alkyl of 1-4 carbon atoms, benzyl, tetrahydropyranyl, or alkanoyl of 1-6 carbon atoms, and Me is an alkali metal atom, with a halide, anhydride, or azide of p-chlorobenzoic acid, in an inert solvent; or c. the cyclization of an o-aminophenylpropionic acid derivative of general Formula V

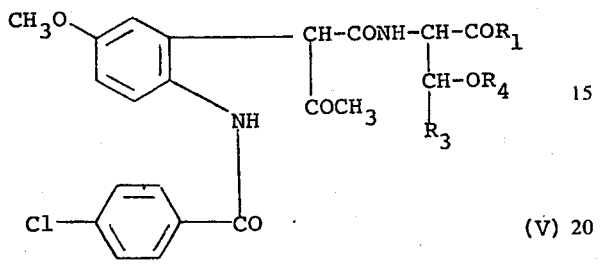

wherein $R_1$, $R_3$ and $R_4$ have the values given above; or d. the cyclization of a phenylhydrazone derivative of general Formula VI

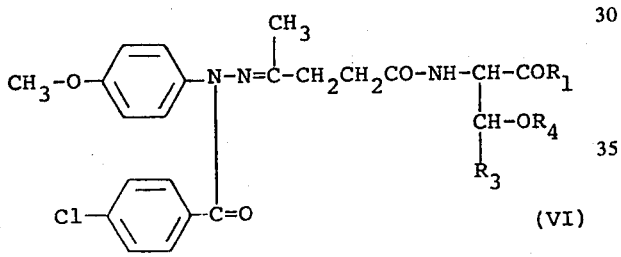

wherein $R_1$, $R_3$ and $R_4$ have the values given above, in the presence of a mineral acid or Lewis acid; and thereafter any protective groups present in the thus-produced compounds are removed and, optionally a thus-produced free acid of general Formula I is reacted with a metal or amine base to form a physiologically acceptable salt thereof or is converted to an ester thereof.

The compounds produced according to alternative (a) of the process of this invention can be synthesized in accordance with conventional methods of peptide linkage as has been described, for example, in the monograph by Jakubke and Jeschkeit, *Aminosaeuren, Peptide, Proteine*, Akademieverlag Berlin (1973), preferably in accordance with mixed anhydride, the chloride, the azide, the carbodiimide, the carbodiimidazole, or the activated-ester method. Polar or non-polar solvents can be used for the condensation process, for example, tetrahydrofuran, dioxane, dimethoxyethane, chloroform, dimethylformamide, dimethylsulfoxide and hexamethylphosphoric acid triamide. In certain cases, the reaction can even be conducted in the presence of water. In order to achieve the linkage of indomethacin derivatives of general Formula II to a free amino acid of Formula III ($R_1$ = OH), it is preferable to use the salt of the latter, formed in situ by the addition of one tertiary base, for example, triethylamine, or N-methylmorphilone. After condensation has been completed, it is possible to obtain the free acid from the salt.

The reaction is carried out at low temperatures, preferably $-20°$ to $-5°$ C., and only in exceptional cases at 0 to $+20°$ C.

Examples of activated indolylacetic acids of the general Formula II are the mixed anhydrides, e.g., mixed with chlorocarbonic acid esters, an internal anhydride, an acid chloride, azide, imidazolide, or an active ester of indolylacetic acid and an activating hydroxy compound such as p-nitrophenol, o-nitrophenol, 2,4-dinitrophenol, 2,4,5-trichlorophenol, pentachlorophenol, pentafluorophenol, N-hydroxysuccinimide, N-hydroxyphenalimide, 1-hydroxybenzotriazole and 3-hydroxy-4-oxo-3,4-dihydro-1,2,3-benzotriazine.

The formation of an activated indolylacetic acid and the formation of a peptide linkage therefrom can take place either simultaneously or subsequent to each other. In general, it is not necessary to isolate the intermediate activated indolylacetic acid.

According to the method employing mixed anhydrides, indomethacin of general Formula II wherein Y = OH is reacted, for example, with a chloroformic (acid) ester in the presence of an organic solvent, such as, for example, tetrahydrofuran, dioxane, chloroform or dimethoxyethane, and in the presence of a base, preferably triethylamine, at temperatures from about $-20°$ to $-10°$ C., thereby forming the mixed anhydride. A solution of a salt, ester, amide, or ether of the general Formula III is then added to the resulting solution dropwise with stirring at the preferred temperatures of $-20°$ to $-10°$ C., mentioned above. The salt solution can be prepared in a mixture of a polar organic solvent and water. The anhydride can be prepared from indomethacin and dehydrating agents, for example, dicyclohexylcarbodiimide, in a polar organic solvent, which can then be reacted with an appropriate amino acid derivative of general Formula III. The reaction can also be carried out in such a way that dicyclohexylcarbodiimide and the amino acid derivative simultaneously react with indomethacin. The preferred temperatures for this reaction are from $0° - 20°$ C. It is also possible to react indomethacin with carbonyldiimidazole in an inert solvent, such as tetrahydrofuran, at temperatures of about $0°$ C., to form imidazolide, which in turn will continue to react with an amino acid derivative of general Formula III.

Other activated indolylacetic acids of Formula II, such as the acid chloride and active esters, can be produced in the usual manner and can then react with amino acid derivatives of Formula III.

The process according to alternative (b) of the present invention can also be carried out in a conventional manner. For example, indolylacetylamino acid derivatives, which differ from those of Formula IV by having a hydrogen atom instead of an alkali metal atom, can be metallized in an anhydrous, inert solvent with an alkali hydride, for example, sodium hydride, and then a halide, preferably the chloride, on the anhydride or azide of p-chlorobenzoic acid is added for reaction at temperatures of $-20°$ C. to $+50°$ C. with the solutions prepared in the said manner.

Suitable anhydrous, inert solvents are, for example, hydrocarbons (such as benzene and toluene), ether (such as diethylether, diisopropylether, tetrahydrofuran, dioxane and 1,2-dimethoxyethane), and dipolar aprotic solvents (such as dimethylformamide and hexamethylphosphoric acid triamide).

The free indolylacetyl amino acid derivatives corresponding to the alkali metal salts of general Formula IV can be prepared in a conventional manner. For example, an active derivative of 5-methoxy-2-methyl-3- indolylacetic acid can be reacted with a serine derivative of general Formula III under the conditions described for alternative (a).

The process according to alternative (c) can also be carried out in a conventional manner. For example, a reactive derivative of β-(2'-nitro-5'methoxyphenyl)-levulinic acid reacts under the conditions of alternative (a) with a serine derivative of general Formula III, to produce a compound of the general Formula VII

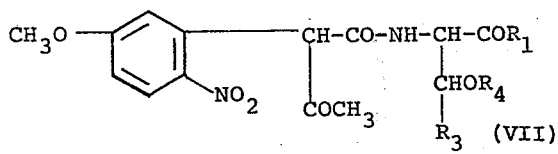

wherein $R_1$, $R_3$ and $R_4$ have the values given above. These compounds can be transformed under the conditions described in German Patent No. 1,470,059 in the presence of p-chlorobenzoylchloride or p-chlorobenzoic acid anhydride into o-aminophenyl propionic acid derivatives of general Formula V, which in turn undergo cyclization under the described conditions to form indole derivatives of general Formula I. Suitable conditions are created, for example, by hydrating the compounds of Formula VII in the presence of nickel-, or palladium-containing hydration catalysts in an inert solvent, such as, for example, an ether, e.g., tetrahydrofuran, dioxane and 1,2-dimethoxyethane.

Alternative (d) of the process of this invention can also be carried out in a conventional manner (R. J. Sundberg, The Chemistry of Indoles, Academic Press, New York and London, 1970).

The reaction uses mineral acids (e.g., hydrochloric acid, sulfuric acid, phosphoric acid), or Lewis acids (e.g., boron trifluoride, zinc chloride), and an inert solvent (e.g., cyclic ethers, lower alcohols and dipolar aprotic solvents).

The starting compounds for this alternative of the process can, for example, be prepared as follows:

A reactive derivative of Levulinic acid reacts with a serine derivative of general Formula III under the conditions defined for alternative (a) to produce a compound of general Formula VIII

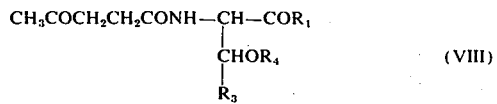

wherein $R_1$, $R_3$ and $R_4$ have the values given above.

Reactive derivatives of levulinic acid can be condensed with p-methoxyphenylhydrazine and acylated with p-chlorobenzoylchloride, to produce compounds of general Formula VI. However, it is also possible to condense compounds of general Formula VIII directly with 1-(4'-methoxyphenyl)-1-(4'-chlorobenzoyl)-hydrazine to produce compounds of general Formula I.

To achieve satisfactory yields in the preparation of indolylacetamino acid derivatives of general Formula I with $R_1$ and/or $R_2$ being a hydrogen atom as defined in alternatives (b), (c) and (d), it is often advantageous to use those compounds of general Formulas IV, V and VI as starting compounds which contain an esterified carboxylic group and/or whose hydroxyl group is protected in the form of tetrahydropyranylether, an alkanoyl ester, or a benzylester, and thereafter split off these protective groups in a conventional manner after the reaction has been completed.

Examples of such compounds of Formula I bearing such protective groups are N-[1-(4-chlorobenzoyl)-5-methoxy-2-methyl-3-indolylacetyl]-serine benzyl ester, O-benzyl ether and benzyl ester, O-benzyl ether. Other examples of other compounds of this invention are N-[1-(4-chlorobenzoyl)-5-methoxy-2-methyl-3-indolylacetyl]serine-amide, -threonine amide, -threonine methyl amide, and -theronine methyl ester and -threonine sodium salt.

Suitable bases for forming physiologically acceptable salts with the compounds of Formula I wherein $R_1$ = OH are physiologically acceptable inorganic and organic bases, such as alkali metal hydroxides, e.g., sodium hydroxide solution, and basic amines, e.g., ethanolamine, diethylamine, N-methylmorpholine, N-dimethylglucamine.

The reaction products are isolated and purified in the usual manner, for example, by extraction and crystallization.

The anti-inflammatory effect of the said compounds was tested in the adjuvant Paw Edema Test. 0.5 mg. of inactivated *mycobacterium butyricum* in 0.1 ml. paraffin of low viscosity were administered as irritant to the right rear paw of male Wistar rats with body weights of 110-160 g. The test animals were treated with a single oral administration of the test compound 1 hour prior to injection of the irritant. The test compounds each were administered in doses of 1 ml per 100 g. of body weight of a suspension consisting of 85 mg. % of Myrj$^{(R)}$53 in a physiological sodium chloride solution. The paw volume was measured 16–40 hours after exposure to irritation. A group of 5 animals each was used per test.

The following Tables (1a) and (1b) give the percentage value of retarding action, calculated according to the formula $$\frac{100 - Y.100}{Z}$$

wherein Y = average difference in paw volume of the treated group and Z = average difference in paw volume of the control group.

TABLE (1a)

| PERCENTAGE OF ADJUVANT RAT PAW EDEMA RETARDATION AFTER ORAL ADMINISTRATION | | | | | | | | |
|---|---|---|---|---|---|---|---|---|
| Dosage | Indomethacin (J) | | J-Methionine* | | J-Serine | | J-Serine-O-Methyl Ether | |
| mole/kg | 16 h | 40 h | 16 h | 40 h | 16 h | 40 h | 16 h | 40 h |
| 2.23 . 10⁻⁶ | 20 | 0 | 22 | 0 | 33 | 10 | 34 | 20 |
| 6.9 . 10⁻⁶ | 43 | 17 | 18 | 0 | 42 | 16 | 43 | 35 |
| 22.3 . 10⁻⁶ | 47 | 46 | 32 | 9 | 48 | 35 | 55 | 37 |

*Japanese Patent 47-44221 (1972); Melting point, our sample, 136°C.

TABLE (1b)

PERCENTAGE OF ADJUVANT RAT PAW EDEMA RETARDATION AFTER ORAL ADMINISTRATION

| Dosage mole/kg | Indomethacin (J) 16 h | Indomethacin (J) 40 h | J-pyrrolidide* 16 h | J-pyrrolidide* 40 h | J-glycinebenzylester* 16 h |
|---|---|---|---|---|---|
| $4.1 \cdot 10^{-6}$ | 28 | 12 | 4 | 0 | 0 |
| $13.9 \cdot 10^{-6}$ | 55 | 40 | 15 | 0 | 8 |
| $41.9 \cdot 10^{-6}$ | 55 | 87 | 30 | 13 | 0 |

*U.S. Pat. No. 3,336,194 (1967).

The tests for bloody epithelium lesions in the stomach were made on rats which had fasted for 16 hours prior to the start of the test and during the 3 hour duration of the said test. The test compound was administered orally in the form of a suspension consisting of 85 mg. % of Myrj$^{(R)}$53 in a physiological sodium chloride solution, in amounts of 1 ml per 100 g. of body weight. The stomach was tested macroscopically 3 hours after the compound had been administered.

Table (2) gives epithelium lesions as mean values based on the following scale:
0 = none,
1 = mild,
2 = serious,
3 = very severe (in limited areas),
4 = very severe (lesions extending throughout the mucous membranes).

(Bibliography: E. Marazi-Uberti, et al., *Arzneimittelforschung* 22 (1a), 191 (1972)).

TABLE (2)

EPITHELIUM LESIONS AFTER 3 HOURS (STOMACH)

| Dosage mole/kg | Indomethacin (J) | J-Serine |
|---|---|---|
| $2.23 \cdot 10^{-6}$ | 0.6 | 0 |
| $6.9 \cdot 10^{-6}$ | 0.6 | 0.2 |
| $22.3 \cdot 10^{-6}$ | 2.0 | 1.0 |

Tables 1 and 2 demonstrate that serine derivatives of indomethacin of this invention are superior to indomethacin and the known indomethacin derivatives which were tested. As shown in Tables 1a and 1b, the novel serine derivatives are more effective retarding agents for inflammation than the known indomethacin derivatives.

Table 2 demonstrates the improved toleration by the stomach of the novel serine derivative compared to indomethacin.

The compounds of general Formula I retard inflammation. In a composition aspect, this invention, therefore, also relates to pharmaceutical compositions comprising at least one compound of general Formula I, including physiologically acceptable salts thereof when $R_1$ is H, in admixture with one or more conventional pharmaceutically acceptable carriers, auxiliary agents and/or diluting agents. The novel compounds can be processed in a conventional manner in order to be used in the form of enteral or parenteral applications. Pills, dragees, capsules, solutions, suppositories, or powders, are suitable forms for enteral administration. Injectionable solutions or suspensions are suitable for parenteral administration. The daily dosage usually ranges from about 20 mg. to about 1 g., preferably from 50–200 mg., the exact dosage being influenced, of course, by the weight of the patient and the receptivity of the particular inflammatory condition for treatment.

In a process aspect, this invention relates to a method of use of a composition of this invention which comprises administering, preferably orally, an anti-inflammatorily effective amount of a compound of Formula I, to a patient with an inflammatory condition.

The compounds of this invention can be administered for the treatment of the same inflammatory conditions and in the same manner as indomethacin and its known derivatives.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

(L)-N-[1-(4-chlorobenzoyl)-5-methoxy-2-methyl-3-indolylacetyl]-serine 1.07 g. of 1(4-chlorobenzoyl)-5-methoxy-2-methyl-3-indolylacetic acid are dissolved in 30 ml. of 1,2-dimethoxyethane and then 0.35 g. of triethylamine is added. The solution is cooled to −10° to −15° C.; 0.4 g. of chloroformic acid isobutylester is then added and the solution is stirred for 30 minutes at about −10°C. Subsequently, a solution of 0.3 g. of (L)-serine in 20 ml. of dimethylformamide and 15 ml. of water to which 0.35 g. of triethylamine has been added, is gradually added drop by drop to the above solution while carefully maintaining the temperature below −10°C. The resulting mixture is stirred for another 30 minutes and the solution is left over night at −15° C.

The solvent is evaporated and the residue is dissolved in chloroform, extracted twice with 2 N HCl, and then washed with water. As the volume of chloroform is reduced by evaporation, the desired product begins to crystallize, is removed by suction and once more suspended in a small volume of chloroform, filtered and dried.

Yield: 0.65 g. (50%)
Melting Point: 190° C.
$[\alpha]_D^{20} = -5.2°$ (c = 0.5; dimethylformamide).

EXAMPLE 2

(D,L)-N-[1-(4-chlorobenzoyl)-5-methoxy-2-methyl-3-indolylacetyl]-O-methyl-serine Preparation as described in Example 1, employing (D,L)-O-methyl-serine.
Yield: 55%
Melting Point: 192° C. (Methanol)

EXAMPLE 3

(D,L)-N-[1-(4-chlorobenzoyl)-5-methoxy-2-methyl-3-indolylacetyl]-serine methyl ester Preparation as described in Example 1, using (D,L)-serine-methyl ester. (The solution of serine ester in dimethylformamide is prepared without the addition of triethylamine or water.)
Yield: 65%
Melting Point: 120° C. (Methanol)

EXAMPLE 4

(D,L)-N-[1-(4-chlorobenzoyl)-5-methoxy-2-methyl-3-indolylacetyl]-serine-methylamide Preparation as described in Example 1, using (D,L)-serine-methylamine. (The solution of serine-methylamine in dimethylformamide is prepared without the addition of triethylamine or water.)
Yield: 60%
Melting Point: 222° C. (Tetrahydrofuran)

EXAMPLE 5

(D,L)-N-[1-(4-chlorobenzoyl)-5-methoxy-2-methyl-3-indolylacetyl]-threonine

Preparation as described in Example 1, using D,L-threonine.
Yield: 50%
Melting Point: 197° C. (chloroform/methanol)

EXAMPLE 6

(D)-N-[1-(4-chlorobenzoyl)-5-methoxy-2-methyl-3-indolylacetyl]-serine

Preparation as described in Example 1, using D-serine.
Yield: 55%
Melting Point: 187° C. (from chloroform)
$[\alpha]_D^{20} = +6°$ (0.5% in dimethylformamide)

EXAMPLE 7

(D,L)-N-[1-(4-chlorobenzoyl)-5-methoxy-2-methyl-3-indolylacetyl]-serine

Preparation as described in Example 1, using D,L-serine.
Yield: 63%
Melting Point: 177° C. (from chloroform)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An indolylacetylamino acid derivative of the formula

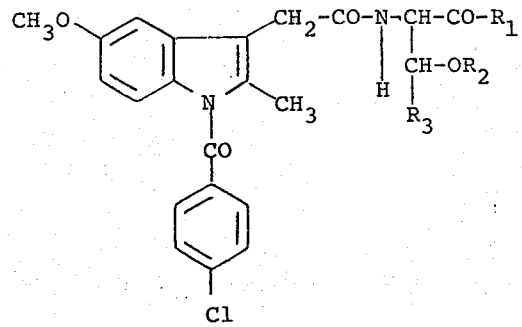

wherein $R_1$ is OH, $NH_2$, $NHR_4$ or $OR_4$, wherein $R_4$ is alkyl of 1–4 carbon atoms, or benzyl; $R_2$ is a hydrogen atom, alkyl of 1–4 carbon atoms, or benzyl; and $R_3$ is a hydrogen atom or methyl, and the physiologically acceptable salts thereof with bases.

2. A compound of claim 1, wherein $R_2$ is H or alkyl.
3. A compound of claim 1, wherein $R_2$ is H.
4. A compound of claim 1, wherein $R_1$ is H, $NHR_4$ or $OR_4$.
5. A compound of claim 4, wherein $R_2$ is H or alkyl.
6. A compound of claim 1, wherein $R_3$ is H.
7. A compound of claim 1, N-[1-(4-chlorobenzoyl)-5-methoxy-2-methyl-3-indolylacetyl]-serine.
8. A compound of claim 1, N-[1-(4-chlorobenzoyl)-5-methoxy-2-methyl-3-indolylacetyl]-O-methyl-serine.
9. A compound of claim 1, N-[1-(4-chlorobenzoyl)-5-methoxy-2-methyl-3-indolylacetyl]-serine methyl ester.
10. A compound of claim 1, N-[1-(4-chlorobenzoyl)-5-methoxy-2-methyl-3-indolylacetyl]-serine methylamide.
11. A compound of claim 1, N-[1-(4-chlorobenzoyl)-5-methoxy-2-methyl-3-indolylacetyl]-threonine.
12. A pharmaceutical composition comprising, in unit dosage form, a compound of claim 1 in admixture with a pharmaceutically acceptable carrier.
13. A method of treating inflammation which comprises administering to a patient with an inflammatory condition, an anti-inflammatory effective amount of a compound of claim 1.

* * * * *